(12) United States Patent
Barker, Jr. et al.

(10) Patent No.: US 8,624,721 B2
(45) Date of Patent: Jan. 7, 2014

(54) METHOD AND APPARATUS FOR EMBEDDING A TRANSMITTER INTO A TOOL, AND A SYSTEM FOR MONITORING THE TOOL

(75) Inventors: Boyd Thomas Barker, Jr., Bartlett, TN (US); Robert Varner, Germantown, TN (US); Jeffrey H. Nycz, Collierville, TN (US); Steven M. Tethrake, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2221 days.

(21) Appl. No.: 11/279,937

(22) Filed: Apr. 17, 2006

(65) Prior Publication Data
US 2007/0244470 A1 Oct. 18, 2007

(51) Int. Cl.
*G08B 1/08* (2006.01)
(52) U.S. Cl.
USPC .................................. 340/539.1; 340/568.1

(58) Field of Classification Search
USPC ........ 340/539.1, 568.1, 10.1, 572.1; 606/170, 606/167
See application file for complete search history.

(56) References Cited

U.S. PATENT DOCUMENTS

| 4,075,632 | A | 2/1978 | Baldwin et al. |
|---|---|---|---|
| 4,360,801 | A | 11/1982 | Duhame |
| 4,390,880 | A | 6/1983 | Henoch |
| 4,739,328 | A | 4/1988 | Koelle et al. |
| 5,030,807 | A | 7/1991 | Landt et al. |
| 2002/0193138 | A1 * | 12/2002 | Chiba et al. ................... 455/550 |
| 2003/0102970 | A1 * | 6/2003 | Creel et al. ................... 340/568.1 |
| 2004/0220602 | A1 * | 11/2004 | Deng et al. ..................... 606/170 |
| 2005/0113037 | A1 * | 5/2005 | Ponce De Leon et al. ... 455/90.3 |
| 2006/0049986 | A1 * | 3/2006 | Dunn et al. ............. 343/700 MS |
| 2006/0244597 | A1 | 11/2006 | Tethrake et al. |

* cited by examiner

*Primary Examiner* — Shirley Lu

(57) ABSTRACT

An apparatus may include a tool having a slot, the tool being composed of an electrical conductor and the slot being formed in an outer wall of the tool. The apparatus may include a transmitter having an antenna, where the antenna may be offset from the tool. The transmitter may be positioned within the slot, may be coupled to the tool by a conductive material, and may be covered with a protective material, where the tool may be adapted to operate as an electrical ground.

20 Claims, 5 Drawing Sheets

METHOD AND APPARATUS FOR EMBEDDING A TRANSMITTER INTO A TOOL, AND A SYSTEM FOR MONITORING THE TOOL

FIELD OF THE INVENTION

The exemplary embodiments may generally relate to management of tools, and may more specifically relate to tracking of tools in supply chain management.

BACKGROUND OF THE INVENTION

Surgical instrument storage and sterilization systems are known. These systems, sometimes referred to as surgical instrument trays or surgical instrument kits, typically include metal or plastic trays that hold a variety of general purpose and/or procedure specific surgical instruments, such as, forceps, scissors, clamps, retractors, scalpels, etc. These trays are brought into the operating room (OR) when preparing for surgery, and also are used as a means to organize, transport, and store surgical instruments in a medical facility.

A primary function provided by surgical trays, in addition to storage, is to facilitate group sterilization. Sterilization is of paramount importance in a surgical setting, such as a hospital, to prevent infecting patients undergoing surgery with potentially deadly infections. Prior to and after every surgical procedure, all surgical instruments and trays must be sterilized before subsequent usage. In order to increase the speed and efficiency of sterilization, entire surgical trays containing several instruments often are placed in a sterilization chamber at once. The sterilization chamber may apply to the trays and to all the instruments contained therein, any combination of heat, pressure, fluid, and/or vaporous sterilant. Sterilization techniques are well known. Thus, a detailed discussion of them has been intentionally omitted.

Because of the need to perform sterilization and the general need to maintain surgical instrument kits in good working order, they often are transported in and out of medical facilities through a distribution center for processing. For example, several surgical instrument kits may be picked up from a hospital or other medical facility at one time. In order to easily and efficiently transport the kits, several kits are placed in a single shipping tote. The shipping tote is a large bin, usually made of plastic or other durable, lightweight material that is able to securely hold two or more instrument kits inside. A worker then may load the shipping totes into a vehicle thereby reducing the number of manual operations that must be performed. Before transporting each shipping tote, a bar coded shipping label is sometimes prepared that identifies certain information such as the point of origin, the destination, and possibly the contents of the tote, i.e., the identification number of each surgical instrument tray contained in the tote. The bar coded label allows the tote to be easily and efficiently tracked and entered into inventory at the receiving facility. These labels are sometimes referred to as "airbills."

Over time, and through ordinary usage, as well as due to rigors of the sterilization process, surgical instruments suffer wear and tear and eventually reach the end of their life cycle. Thus, it is necessary to periodically inspect and maintain records on usage of surgical instruments so that they can be replaced as necessary. Also, due to the fact that they are constantly moved from the operating room to sterilization, to storage through processing facilities, and back to the operating room, various instruments on a given tray may become lost. Because certain instruments are so specialized that they have no functional substitutes, it also has become necessary to regularly inspect trays and to readily identify specific instruments that are missing.

Existing technology for uniquely marking surgical instruments for identification is based upon visual markings, bar coding, or two-dimensional (2D) matrix (micro-dots) marking. These technologies are limited by being orientation restrictive, highly manual, require complex manufacturing processes, or are intrusive to the user of the instrument. Moreover, existing methods for performing these necessary identification functions are overly reliant on costly human interpretation. In some cases, a skilled technician may be required to identify the surgical instruments, which keeps the skilled technician from performing other valuable functions.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

There is a need for a non-manual system for processing and managing medical and non-medical instruments.

Exemplary embodiments may include a method and an apparatus for integrating a transmitter into a tool, and may include a system for monitoring a tool having an integrated transmitter.

An apparatus according to exemplary embodiments may include a tool having a slot, the tool being composed of an electrical conductor, the slot being formed in an outer wall of the tool, and a transmitter having an antenna, the antenna being offset from the tool, the transmitter being positioned within the slot, being coupled to the tool by a conductive material, and being covered with a protective material, wherein the tool is adapted to operate as an electrical ground.

A method according to exemplary embodiments may include forming a slot in an outer wall of a tool, the tool being composed of an electrical conductor, positioning a transmitter within the slot, the transmitter comprising an antenna, affixing the transmitter to the tool with a conductive material, and covering the transmitter with a protective material, wherein the antenna is offset from the tool.

A system according to exemplary embodiments may include an access point, a tool being composed of an electrical conductor and having a slot, the slot being formed in an outer wall of the tool, and a transmitter having an antenna, the antenna being offset from the tool, the transmitter being positioned within the slot, being coupled to the tool by a conductive material, and being covered with a protective material.

BRIEF DESCRIPTION OF THE DRAWINGS

Purposes and advantages of the exemplary embodiments will be apparent to those of ordinary skill in the art from the following detailed description in conjunction with the appended drawings in which like reference characters are used to indicate like elements, and in which.

Figure 1:
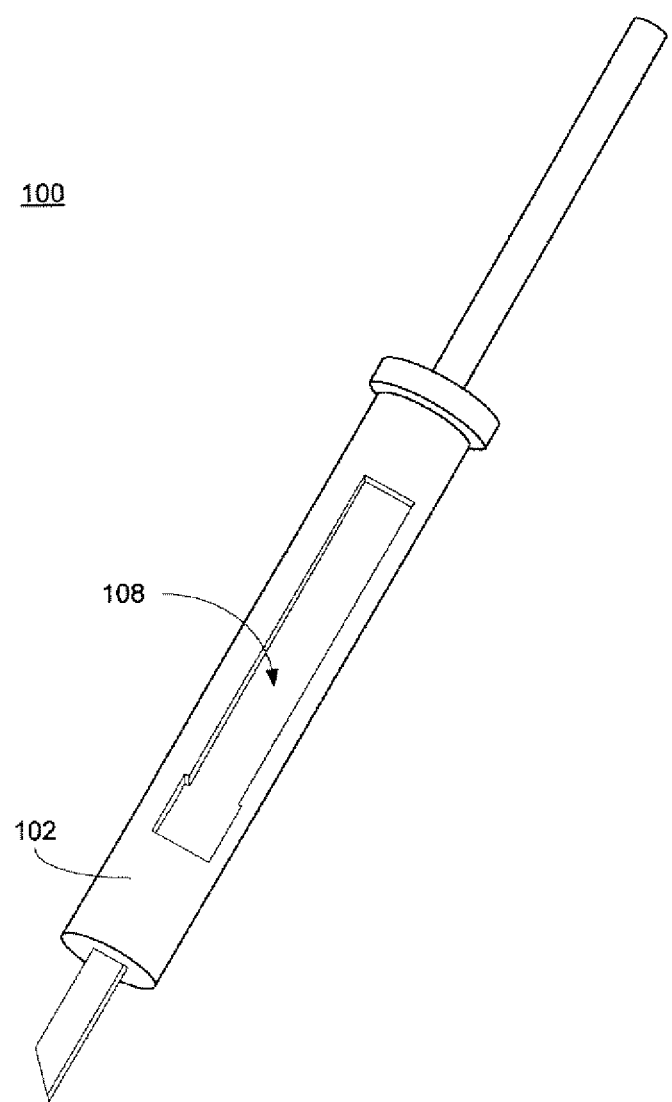
FIG. 1 illustrates an exemplary embodiment of a tool having a slot before a transmitter is placed in the slot.

These and other embodiments and advantages will become apparent from the following detailed description, taken in conjunction with the accompanying drawings, illustrating by way of example the principles of the various exemplary embodiments.

DETAILED DESCRIPTION OF EXEMPLARY EMBODIMENTS

The following description is intended to convey a thorough understanding of the exemplary embodiments by providing a number of specific exemplary embodiments and details involving exemplary methods and apparatuses for embedding a transmitter into a tool and exemplary systems for communicating with tools having an embedded transmitter. It should be appreciated, however, that the exemplary embodiments are not limited to these specific embodiments and details. It is further understood that one possessing ordinary skill in the art, in light of known systems, methods, and apparatuses, would appreciate the use of the exemplary embodiments for their intended purposes and benefits in any number of alternative embodiments, depending upon specific design and other needs.

The terminology used herein is for the purpose of describing particular embodiments only and is not intended to limit the scope of the exemplary embodiments. As used throughout this disclosure, the singular forms "a," "an," and "the" include plural reference unless the context clearly dictates otherwise. Thus, for example, a reference to "a tool" includes a plurality of such tools, as well as a single tool, and a reference to "an instrument" is a reference to one or more instruments and equivalents thereof known to those skilled in the art, and so forth.

Unless defined otherwise, all technical and scientific terms used herein have the same meanings as commonly understood by one of ordinary skill in the art to which this invention belongs. All publications mentioned herein are cited for the purpose of describing and disclosing the various implants, prosthesis, components, methods of implantation, coatings and surface treatments, and other components that are reported in the publications that might be used in connection with the embodiments. Nothing herein is to be construed as an admission that the embodiments described herein are not entitled to antedate such disclosures by virtue of prior invention.

As used herein, the expressions and terms "surgical instrument," "surgical tool," "instrument," or "tool" will refer to any type of surgical or medical instrument or portable equipment or device to which it may be desirable to attach a transmitter, such as, but not limited to, a radio frequency identification (RFID) tag. Though the specification is written in the context of medical and/or surgical instruments, it should be appreciated that the transmitter of the exemplary embodiments may be used with a variety of different items to be identified as shape and design constraints permit, including tools and equipment in other fields unrelated to the medical field. This may include hand tools or other objects and/or equipment that are used in construction, manufacturing, maintenance, automotive, consumer, aviation, or other similar and differing industries.

The exemplary embodiments may generally relate to placing a transmitter below the surface of a tool, such as, but not limited to, a surgical instrument or other metal tools or utensils, and encapsulating the transmitter in a protective material. In an exemplary embodiment, natural conductive properties of the metal instrument may allow a transmitter, such as, but not limited to, a Ultra-High Frequency (UHF) transmitter or a Microwave RFID) tag, to be completely embedded below the metal surface of the tool and also may allow the transmitter to communicate identification information about the tool.

The exemplary embodiments also may overcome problems with embedding a transmitter in a metal tool. Simply embedding a transmitter within a metal instrument may be problematic for at least the following three reasons. First, conventional transmitter form factors may not be designed for use with very small diameter or thin surface tools, which may frequently occur in surgical instruments.

Second, embedding a transmitter operating at radio frequency (RF), ultra-high frequency (UHF), and microwave frequencies in an electrical conductor may severely detune the performance of the transmitter. Detuning may generally refer to a degradation in performance of the transmitter. Detuning may occur because the electrical conductor absorbs and reflects electromagnetic wireless signals, which may modify the frequency of the wireless signal. This may cause problems when a wireless reader device expects to receive a wireless signal from the transmitter within a certain frequency band, and, because of the electrical conductor, the modified frequency of the wireless signal may fall outside of the frequency band and may not be detected by the wireless reader device.

Third, affixing a transmitter to a surgical instrument may be problematic due to the sterilization requirements of surgical instruments, and the specialty of surgical instruments may limit any changes that may affect the aesthetics, function, or ergonomics of the instruments for users. Exemplary embodiments overcome transmitter design limitations allowing for a very small, low profile transmitter that performs highly while embedded within a metal tool.

Exemplary embodiments are initially discussed with reference to FIG. 1. FIG. 1 illustrates an exemplary embodiment of a tool 100 having a slot 108 prior to placing a transmitter 104 (see FIG. 2) in the slot 108. The tool 100 may be a surgical tool, such as, but not limited to, a scalpel useable during surgery, or other types of surgical and non-surgical tools. The tool 100 also may be of other sizes and shapes, as will be appreciated by those skilled in the art. The slot 108 may be formed in an outer wall of a body 102 of the tool 100. In various exemplary embodiments, the body 102 may be composed of an electrical conductor. Any electrical conductor, such as, but not limited to, a metal, surgical stainless steel, titanium, or other known electrical conductors may be used. The slot 108 may form a depression beneath the surface of the outer wall of the body 102. The slot 108 may be formed using any machining mechanical process that etches into the body 102. Alternatively, a tool die may form the slot 108 when the tool 100 is manufactured.

Figure 2:
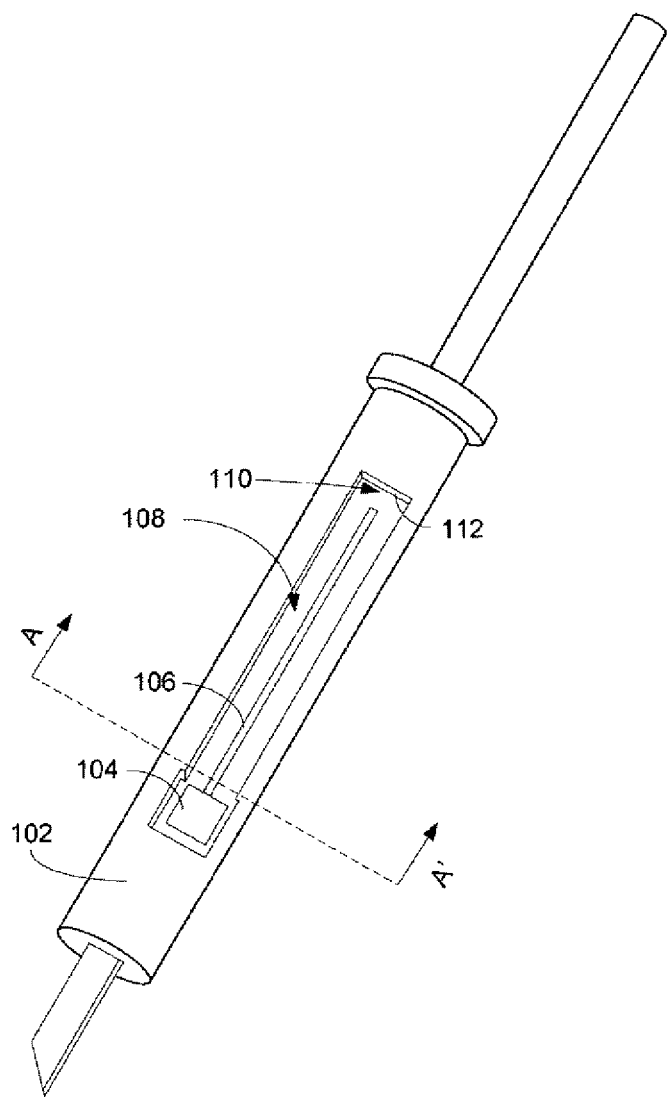
FIG. 2 illustrates an exemplary embodiment of a tool having a slot after a transmitter is placed in the slot.

FIG. 2 illustrates an exemplary embodiment of the tool 100 with a transmitter 104 placed in the slot 108. The transmitter 104 may be any device capable of wirelessly communicating RF, UHF, microwave frequency signals, or other wireless signals capable of containing information. The transmitter 104 may be a miniature electronic circuit that may include a microprocessor. The transmitter 104 may be adapted to wirelessly communicate in various wireless environments. Various wireless environments may include responding to a RF signal emitted from a RF field generator, where, upon receipt of the RF signal, the transmitter 104 may transmit a wireless response signal with information about the transmitter 104.

Alternatively, the RF signal may be a RF field. The transmitter 104 may be referred to as passive in this wireless environment, where the transmitter 104 only transmits a signal after receiving a signal from another source. Alternatively, the transmitter 104 may be active and periodically or aperiodically transmit signals. In various exemplary embodiments, the transmitter 104 may be wireless signal powered (also referred to as beam powered), where power from a received wireless signal may energize circuitry of the transmitter 104 and may cause the transmitter 104 to perform a data operation, such as, but not limited to, emitting a wireless signal.

In an exemplary embodiment, the transmitter 104 may include an RFID tag. The basic structure and operation of RFID tags can be found in, for example, U.S. Pat. Nos. 4,075,632, 4,360,801, 4,390,880, 4,739,328 and 5,030,807, the disclosures of which are incorporated herein by reference in their entireties. RFID tags also may be described in co-pending U.S. patent application Ser. No. 11/341,489, titled "Surgical Instrument Tray RFID Tag," filed Jan. 30, 2006, the contents of which are incorporated herein by reference in their entirety. In various exemplary embodiments, the transmitter 104 may be state machine oriented, have global lock capability, write to every non-locked byte, have multiple functions, write to one byte individually, have bulk write capability, have group select capability, be anti-collision capable (e.g., may sort X number of transmitters per second), have cyclic redundancy check (CRC) 16 messaging, operate over −40° C. to +85° C., and may have high speed operation. The transmitter 104 may have other features, and/or combinations of one or more of these features, as will be appreciated by those skilled in the art.

The transmitter 104 may transmit data within specified frequency bands that conform to regulatory standards for the country in which the transmitter 104 is used. In various exemplary embodiments, the transmitter 104 may operate in the frequency band of 860-960 MHz. Alternatively, the transmitter 104 may operate at other frequency bands. Transmission within the frequency bands also may conform with the regulatory standards of the host country or the needs of the system, as will be appreciated by those skilled in the art.

The transmitter 104 may generally be rugged enough to survive typical use in a surgical environment. The transmitter 104 may be designed to survive multiple sterilization cycles that tools in a surgical environment may be exposed to, such as, but not limited to, autoclaving and citric passivation baths. Alternatively, the transmitter 104 may be designed to survive other harsh environments. Various exemplary embodiments may permit the transmitter 104 to survive harsh environments to which the tool 100 may be exposed, such as, but not limited to, extreme temperatures, high pressure, vibrations, droppage of the tool 100, and harsh chemicals.

The transmitter 104 also may include a memory. The memory may include read/write functionality, which may allow certain stored information in the memory to be altered, re-evaluated, and read. The memory may have both locked and unlocked memory. Generally, the locked portion of the memory may be read only, and may not be changed without physically reprogramming the memory. The locked portion of the memory may store a unique identification number for identifying the transmitter 104 that corresponds to the tool 100. The unique identification number may be used to index a database containing price, product name, manufacturer, and/or other information that may be used to track the tool 100 over its life cycle.

The unlocked portion of the memory may store information on events occurring in the life cycle of the tool 100. This information may include, but is not limited to, the number of times the tool has been used, identification numbers of the surgery in which the tool 100 was used, the number of times the tool 100 has been sterilized, the dates of inspection of the tool 100, the operator who performed the inspection of the tool 100, the name of the surgeon who performed surgery with the tool 100, the location at which the tool 100 was last scanned, the names of the locations or hospitals where the tool 100 had been used, and/or other information that may be used to track the travel, usage, storage, and inspection of the tool 100 over its life cycle.

Figure 3:
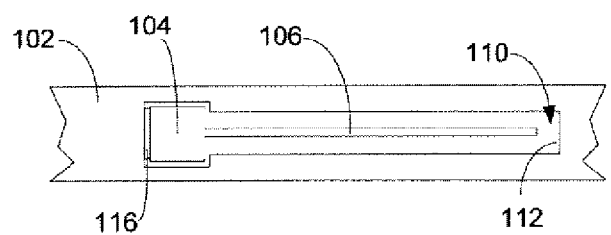
FIG. 3 illustrates a partial side view of an exemplary embodiment of a transmitter placed in a slot of a tool.

FIG. 3 depicts a partial side view of an exemplary embodiment of the transmitter 104 within the slot of the tool 100. During manufacturing of the tool 100, the transmitter 104 may be inserted into the slot 108 after the slot 108 is formed in the tool 100. In various exemplary embodiments, the transmitter 104 may have dual poles. A first of the dual poles of the transmitter 104 may be directly affixed to an inner wall 116 of the slot 108 with a conductive material or a conductive snap. The conductive material may be solder, a conductive epoxy, or any other suitable material to allow electrical current to flow between the body 102 of the tool 100 and the transmitter 104. In an exemplary alternative embodiment, the transmitter 104 may be formed on a circuit board that has a pin that may be coupled to the inner wall 116 of the tool 100.

Attached at a second of the dual poles, the transmitter 104 may have a short, thin gauge, conductive antenna 106. The antenna 106 may be adapted to radiate and/or emit a wireless signal generated by the transmitter 104. The antenna 106 may be an antenna wire and may be circularly polarized or linearly polarized. In various exemplary embodiments, the antenna wire may be 30 aught magnetic wire. The antenna 106 may be made of a variety of conductive materials. Materials such as, but not limited to, conductive inks, wire trace (e.g., copper, silver, gold, etc.), and/or any conductive metal wire may be used as the conductive portion of the antenna.

During insertion of the transmitter 104, the antenna 106 may be positioned within the slot 108 such that the antenna 106 is offset from contacting any metal surrounding the slot 108. In other words, the antenna 106 may be positioned within the slot 108 so that no portion of the antenna 106 electrically contacts any wall of the slot 108. A gap 110 may be located between the end of the antenna 106 and wall 112 of the slot 108. The gap 110 may be a space between the end of the antenna 108 and the wall 112 so that the antenna 106 may not electrically contact the wall 112. Thus, the only point of electrical contact of the transmitter 104 with the body 102 may be at the inner wall 116.

Figure 4A:
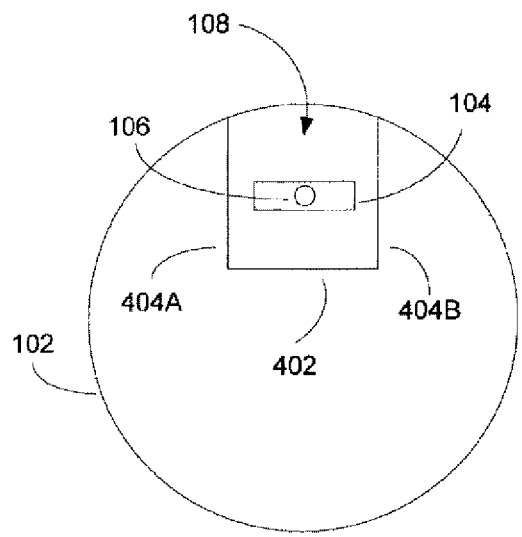
FIGS. 4A-B illustrate cross-sectional views of an exemplary embodiment of a tool with a transmitter embedded in a slot.

FIG. 4A illustrates a cross-sectional view along line A-A' in FIG. 2 of an exemplary embodiment of the transmitter 104 embedded within the slot 108. As depicted, the transmitter 104 may be positioned within the slot 108 of the body 102 of the tool 100 below the outer surface of the body 102. The antenna 106 may be positioned within the slot 108 so that it does not contact side walls 404A-B or base wall 402.

Figure 4B:
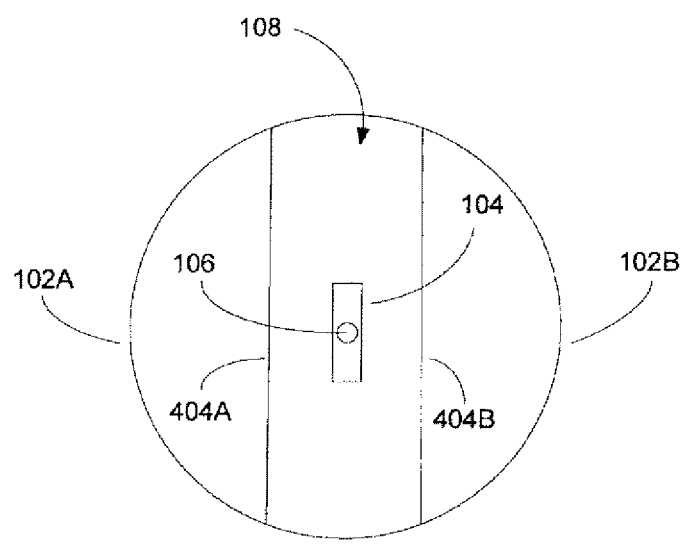

FIG. 4B illustrates a cross-sectional view along line A-A' in FIG. 2 of an alternative exemplary embodiment of the transmitter 104 embedded within the slot 108. As depicted, the transmitter 104 may be positioned within the slot 108 of the body 102 of the tool 100 below the outer surface of the body 102. In this embodiment, the slot 108 may extends laterally through the body 102, thus forming a hole through the body 102 of the tool 100 that is bounded by body halves 102A and 102B. The slot 108 may have other sizes and shapes, as will be appreciated by those of skill in the art. Forming the slot 108 laterally through the body 102 may permit the transmitter 104 to emit a wireless signal that is receivable over 360° relative to a longitudinal axis of the tool 300, which may not occur in the slot 108 of FIG. 4A because of base wall 402. Additionally, having the slot 108 laterally formed through the body 102 may permit the transmitter 104 to be embedded deeper within the body 102.

The transmitter 104 may be quickly affixed within the slot 108 on the tool 100 prior to covering the transmitter 104 with a protective material. Once the transmitter 104 is inserted into the slot 108 and affixed to the body 102 at the inner wall 116, the transmitter 104 and the antenna 106 then may be completely covered and/or sealed with a protective material, such as, but not limited to, a non-conductive material, such as, but not limited to, an epoxy, a silicone, a plastic, a rubber, or other non-conductive materials. The protective material may be visually clear, opaque, or be of a desired color, and may be adapted to withstand multiple sterilization cycles, such as, but not limited to, repeat autoclave cycles and citric passivation baths. The protective material also may protect the transmitter 104 from harsh chemicals during sterilization. Covering the transmitter 104 also may be referred to as overmolding or encapsulating. The protective material may cover the transmitter 104 such that the transmitter 104 may be embedded below the surface of the body 102 of the tool 100 and sealed. In an alternative exemplary embodiment, the transmitter 104 may not completely be embedded below the surface of the body 102 of the tool 100. This may occur at an area of the tool 100 where there is low potential risk for the transmitter 104 being damaged or unintentionally removed or where the transmitter 104 does not interfere with an operator's use of the tool 100. The protective material may protect the transmitter 104 as well as hold the transmitter 104 and the antenna 106 in place. Generally, the protective material may insulate the transmitter 104 and the dielectric properties of the protective material may permit energy from wireless signals to propagate through the protective material.

Once covered, the protective material may be processed so that the contour of the protective material substantially corresponds to the shape of the body 102 of the tool 100. For example, FIG. 2 illustrates the body 102 having a substantially cylindrical shape. The slot 108 may be filled with the protective material to correspond to the contour of the cylindrical shape of the body 102 (also see FIGS. 4A-B). The protective material may be made from a material capable of being shaped after filling the slot 108 so that the contour matches the contour of the body 102. The body 102 and the slot 108 may be of other geometric, asymmetrical, symmetrical, or other desired shapes, as will be appreciated by those skilled in the art.

Embedding the transmitter 104 in the tool 100 may provide advantages due to the conductive properties of the tool 100. When the transmitter 104 emits a wireless signal, such as, but not limited to a UHF, RF, or, microwave signal, the transmitter 104 may utilize the metal in the tool 100 as an electrical ground plane, thus making the tool 100 a part of the antenna circuit. This may allow the antenna 106 to be much smaller than would typically be required to operate at UHF and microwave frequencies while still allowing the antenna 106 to resonate. Using the tool 100 as the ground plane minimizes detuning of the transmitter 104 as the tool 100 is held in differing ways during transmission by the transmitter 104. Minimizing detuning may imply that the antenna 106 may be efficient and the electrical current flow may not be countering or cancelling out. The design of the antenna 106 may account for the effects of the dielectric properties of the protective material, the type of material selected for the antenna 106, the overall size of the antenna 106, the amount of protective material, the size of the tool 100, and other properties and sizes of the components of the tool 100. The antenna 106 also may allow for anti surface-current cancellation (same current direction), have a fully-radiated antenna design, have a dipole-like radiation pattern, and have a multiband return-loss response.

The design of the antenna 106 may depend upon the size of the tool 100, the frequency of operation, and environmental conditions. The antenna 106 may be very small, less than one square inch or much larger, depending upon the operational requirements. For example, if the antenna 106 were placed in the slot 108 with an offset of approximately 0.010-0.020 inches from the walls of the slot 108 and the slot 108 filled with the protective material, the overall length of the antenna 106 at 915 MHz (UHF) may be 1.0-1.5 inches long, and at 2.45 Ghz (Microwave), the antenna 106 may be 0.5-1.0 inches long. In general, the length of the electromagnetic wave may affect the antenna design. The design may have the electrical length of the antenna 106 equal to the wavelength of the electromagnetic wave. The length of the antenna 106 also may be a fraction of the length of the wavelength. For example, the length of the antenna 106 may be a quarter or an eighth of the wavelength. Other fractions of the length of the antenna 106 compared to the length of the wavelength may be used. Having the antenna 106 operating at RF, UHF, microwave, or other operating frequencies may allow a wireless reader device to wirelessly receive information from multiple transmitters 104 at the same time, may improve the distance over which wireless signals may be received from the transmitter 104, and may prevent data collisions from multiple transmitters 104 simultaneously transmitting.

Figure 5:
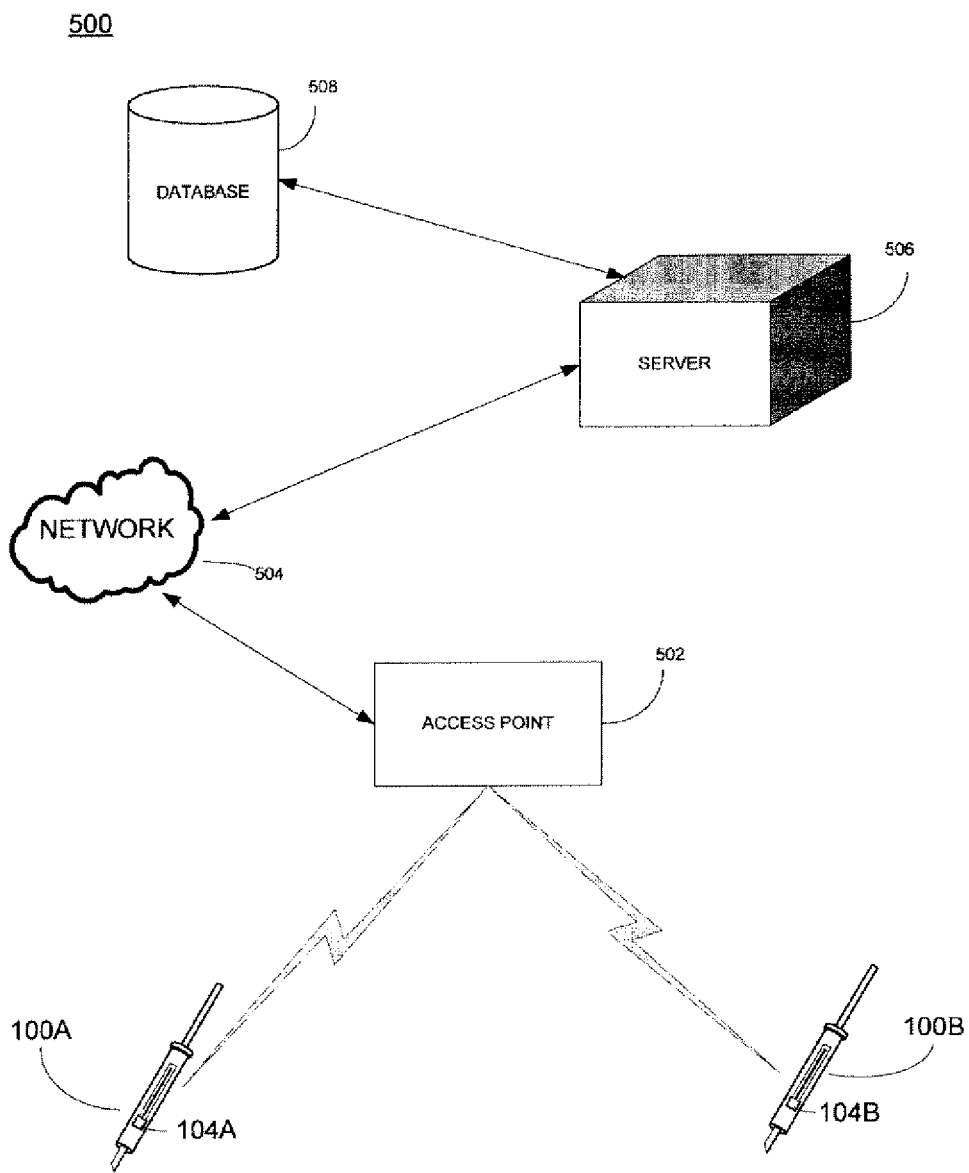
FIG. 5 illustrates an exemplary embodiment of a system monitoring a tool having an embedded transmitter.

FIG. 5 illustrates an exemplary embodiment of a system 500 communicating with tools 100A-B having respectively embedded transmitters 104A-B. In the depicted embodiment, the system 500 may include one or more tools 100A-B, an Access Point 502, a Network 504, a Server 506, and a Database 508. In an alternative embodiment, the tools 100A-B may be arranged on a tray, or may be placed within a container. The depicted number of components in the system 500 is exemplary. The system 500 may include more or less components, such as more or less tools 100, as will be appreciated by those skilled in the art. The system 500 may respectively allow transmitters 104A-B associated with the tools 100A-B to wirelessly communicate information through the Access Point 502 and the Network 504 to the Server 506 and the Database 508. The Access Point 502 may directly connect to the Network 504, or may connect through a local area network (LAN), a wireless LAN (WLAN), an Internet Service Provider (ISP), or other methods for connecting to a network, which are known and are omitted for brevity.

The Access Point 502 may be a computing device that wirelessly communicates with the transmitters 104A-B. In various exemplary embodiments, the Access Point 502 may be a wireless reader device and may include an RF field generator (reader) to wirelessly extract identification information, such as, but not limited to, a Universal Product Code (UPC), a product name, a unique identification number, or other information stored in the locked and unlocked portions of the memory of the transmitter 104. The Access Point 502 also may comply with the regulatory standards of the host country. For example, in the United States and in North America, RF field generators may conform with Federal Communications Commission (FCC) unlicensed requirements, such as FCC Part 15. Europe sets similar standards, such as ETSI 300.400 869 MHz operation. Other countries may recognize either FCC or ETSI requirements or require the RF field generators to meet different requirements. One of ordinary skill in the art will appreciate that it is within the scope of the various exemplary embodiments that the transmitter 104 and the Access Point 502 may be modified to meet various regulatory requirements of the host country.

In an exemplary embodiment in a surgical environment, tools 100A-B may be placed on a tray and may be sent through a RF field generated by the Access Point 502. Alternatively, the Access Point 502 may generate a RF signal. When the transmitters 104A-B of the tools 100A-B enter the RF field, the RF field may energize circuitry of the transmitters 104A-B and may cause the circuitry to perform a data operation. In various exemplary embodiments, the data operation may cause the transmitter 104 to transmit a wireless response signal, such as, but not limited to, a RF or UHF signal, containing extraction data. The extraction data may include the identification information stored in the locked portion of the memory of the transmitter 104, and/or may include information stored in the unlocked portion of the memory. Alternatively, the RF field generated by the Access Point 502 also may communicate update information to the transmitter 104 for storage in the unlocked portion of the memory of the transmitter 104.

After the Access Point 502 receives the response wireless signal containing the identification information from the transmitter 104, the Access Point 502 may communicate this information to the Server 506, the Database 508, or both. The identification information may be used to track the tool 100 to determine its location, to determine if the tool 100 has been placed on the wrong tray, to track the number of uses of the tool 100, or other information about the tool over its life cycle. The Server 506 and/or the Database 508 may include a database table that stores information on each tool 100 similar to the information stored in the locked and unlocked portions of the memory of the transmitter 104. Additionally, the database table also may store information for managing and tracking the tool 100 over its life cycle.

In a surgical environment, the Server 506, the Database 508, or both may review the identification information from one or more tools 100 communicated from the Access Point 502 to identify if the one or more tools 100 correspond to different manufacturers or sterilization processors. This may be beneficial since manufacturers or sterilization processors typically only service and sterilize their own tools. After reviewing the identification information from the one or more tools, the Server 506, the Database 508, or both, may, for example, communicate a signal for display to an operator at the Access Point 502 indicating that a tool is missing from the tray, that all tools are accounted for, that a tool is improperly included on the tray that belongs to a different manufacturer than the other tools, or other information that the operator may use to process the tool 100. Thus, the transmitters 104A-B embedded in the respective tools 100A-B may prevent the one or more tools 100 from improperly being sent to the wrong manufacturers or sterilization processors. Moreover, this information may be used to identify if any tools are missing from the tray. Thus, the exemplary embodiments may save time in identifying tools and may prevent the loss of tools, while being able to withstand the processing rigors that the tools may experience.

Therefore, embedding the transmitter 104 in the toot 100 may not affect the physical appearance, aesthetics, function, or ergonomics of the instruments for users. When covered with the protective material, the transmitter 104 may be invisible or unobtrusive to the user of the tool 100, but still allow for rapid, accurate, automatic, non-orientation restrictive identification and processing of the tool 100 in various processes of supply chain usages, as well as in tracking and managing use of the tool over its life cycle.

The exemplary embodiments described herein are not to be limited in scope by the specific exemplary embodiments discussed. For example, although many of the embodiments disclosed herein have been described with reference to surgical instruments, the principles described herein are equally applicable to tracking and monitoring conductive instruments in other environments, such as, but not limited to, automotive, aviation, consumer, and other industries that track the use, maintenance, and location of instruments, tools, and utensils. Indeed, various modifications of the exemplary embodiments, in addition to those described herein, will be apparent to those of ordinary skill in the art from the foregoing description and accompanying drawings. Thus, such modifications are intended to fall within the scope of the embodiments. Further, although some of the exemplary embodiments have been described herein in the context of a particular implementation in a particular environment for a particular purpose, those of ordinary skill in the art will recognize that its usefulness is not limited thereto and that the exemplary embodiments can be beneficially implemented in any number of environments for any number of purposes.

The invention claimed is:

1. An apparatus comprising:
   a surgical tool having a slot, the tool being composed of an electrical conductor, the slot being formed in an outer wall of a conductive portion of the tool; and
   a transmitter comprising an antenna, the antenna being offset from the tool, the transmitter being positioned within the slot, the transmitter being coupled to the conductive portion of the tool by a conductive material, and the transmitter being covered with a protective material, wherein the tool is adapted to operate as an electrical ground.

2. The apparatus of claim 1, wherein the electrical conductor is composed of metal, titanium, and/or surgical stainless steel.

3. The apparatus of claim 1, wherein the conductive material is one of solder or a conductive epoxy.

4. The apparatus of claim 1, wherein the protective material is non-conductive and comprises at least one of epoxy, silicone, plastic, or rubber.

5. The apparatus of claim 1, wherein the antenna is adapted to radiate a wireless signal.

6. The apparatus of claim 5, wherein the transmitter is adapted to transmit the wireless signal after receiving a radio frequency signal.

7. The apparatus of claim 1, wherein the transmitter comprises a radio frequency identification (RFID) tag.

8. The apparatus of claim 1, wherein the transmitter comprises a memory, the memory being adapted to store a unique identification number.

9. The apparatus of claim 1, where the slot laterally extends through the tool.

10. The apparatus of claim 1, wherein the tool further comprises:
    a bottom wall, wherein the bottom wall bounds the slot.

11. The apparatus of claim 1, wherein the transmitter is adapted to wirelessly communicate with a computing device.

12. The apparatus of claim 1, further comprising:
    a circuit board comprising a pin, wherein the transmitter is coupled to the circuit board.

13. A method comprising:
    forming a slot in an outer wall of a conductive portion of a surgical tool, the tool being composed of an electrical conductor;
    positioning a transmitter within the slot, the transmitter comprising an antenna;

affixing the transmitter to the conductive portion of the tool with a conductive material; and covering the transmitter with a protective material, wherein the antenna is offset from the tool.

14. A system comprising:

an access point;

a surgical tool being composed of an electrical conductor and having a slot, the slot being formed in an outer wall of a conductive portion of the tool; and a transmitter comprising an antenna, the antenna being offset from the tool, the transmitter being positioned within the slot, the transmitter being coupled to the conductive portion of the tool by a conductive material, and the transmitter being covered with a protective material.

15. The system of claim 14, wherein the transmitter is adapted to wirelessly communicate with the access point.

16. The system of claim 14, wherein the transmitter is adapted to transmit a wireless signal after receiving a radio frequency signal generated by the access point.

17. The system according to claim 16, wherein the transmitter further comprises:

a memory, wherein the radio frequency signal contains update information writeable to the memory.

18. The system of claim 16, further comprising:

a server, wherein the access point receives the wireless signal and the server receives extraction data based on the wireless signal from the access point across a network.

19. The system of claim 18, wherein the server is adapted to transmit update data across the network to the access point.

20. The system according to claim 19, wherein the access point is adapted to transmit the update data to the transmitter.

* * * * *